US006963286B2

(12) United States Patent
Marquis et al.

(10) Patent No.: US 6,963,286 B2
(45) Date of Patent: Nov. 8, 2005

(54) WHEELCHAIR AND ALARM THEREFOR

(75) Inventors: James A. Marquis, Warwick, RI (US); James K. Ritchie, Waterford, CT (US)

(73) Assignee: 210 Innovations LLC, Waterford, CT (US)

( * ) Notice: Subject to any disclaimer, the term of this patent is extended or adjusted under 35 U.S.C. 154(b) by 106 days.

(21) Appl. No.: 10/352,154

(22) Filed: Jan. 28, 2003

(65) Prior Publication Data

US 2003/0169175 A1 Sep. 11, 2003

Related U.S. Application Data

(60) Provisional application No. 60/360,047, filed on Feb. 27, 2002.

(51) Int. Cl.⁷ .............................................. G08B 21/00
(52) U.S. Cl. .................... 340/666; 340/667; 340/686.1; 340/614; 340/691.6; 340/692; 280/304.1; 280/250.1
(58) Field of Search ................................ 340/666, 667, 340/686.1, 614, 691.6, 692; 280/304.1, 250.1

(56) References Cited

U.S. PATENT DOCUMENTS

| 3,903,513 A | 9/1975 | Green et al. |
| 4,536,755 A | 8/1985 | Holzgang et al. |
| 4,638,307 A | 1/1987 | Swartout |
| 4,858,622 A | 8/1989 | Osterweil |
| 5,052,065 A | 10/1991 | West |
| 5,203,433 A | 4/1993 | Dugas |
| 5,335,741 A | * 8/1994 | Rabinovitz et al. .......... 180/8.2 |
| 5,358,266 A | 10/1994 | Roth et al. |
| 5,471,198 A | 11/1995 | Newham |
| 5,494,046 A | 2/1996 | Cross |
| 5,654,694 A | 8/1997 | Newham |
| 5,990,799 A | 11/1999 | Boon et al. |
| 6,025,782 A | 2/2000 | Newham |
| 6,049,281 A | 4/2000 | Osterweil |
| 6,092,824 A | 7/2000 | Ritchie et al. |
| 6,163,249 A | 12/2000 | Betcher, III |
| 6,166,644 A | 12/2000 | Stroda |
| 6,204,767 B1 | 3/2001 | Sparks |
| 6,239,704 B1 | 5/2001 | Olson |
| 6,279,936 B1 | 8/2001 | Ritchie et al. |
| 6,297,738 B1 | 10/2001 | Newham |
| 6,371,503 B2 | 4/2002 | Ritchie et al. |
| 2001/0001237 A1 | 5/2001 | Stroda et al. |
| 2001/0040354 A1 | 11/2001 | Ritchie et al. |
| 2002/0067273 A1 | 6/2002 | Jaques et al. |
| 2002/0070866 A1 | 6/2002 | Newham |
| 2002/0070867 A1 | 6/2002 | Conway et al. |

OTHER PUBLICATIONS

AliMed Patient Care, Winter 1999–2000, including but not limited to the QualCare Alarm Cushions (p. 4), pp. 3–4.
AliMed Patient Care, Summer 1999, including but not limited to #k87851 Drainage Bag Holder (p. 2), pp. 1–2.
Fall Management, Restraint–free fall prevention; Issue 3, Year 2000; pp. 1, 9, 11, 29, and 30.

* cited by examiner

*Primary Examiner*—Tai Nguyen
(74) *Attorney, Agent, or Firm*—Miele Law Group; Anthony L. Miele

(57) ABSTRACT

The present invention relates to a wheelchair and an under-seat alarm system therefor.

22 Claims, 2 Drawing Sheets

WHEELCHAIR AND ALARM THEREFOR

The present application claims priority to U.S. Provisional Appln. Ser. No. 60/360,047, filed Feb. 27, 2002, the entirety of which is hereby incorporated into the present application by reference.

FIELD OF THE INVENTION

The present invention relates to a wheelchair and an underseat alarm system therefor.

BACKGROUND OF THE INVENTION

U.S. Pat. No. 3,903,513 discloses an underseat wheelchair alarm system. The construction disclosed therein, however, is not well suited for practical use. Specifically, it does not allow the wheelchair to be collapsed to a storage position when not in use, without removing the alarm system.

SUMMARY OF THE INVENTION

One aspect of the present invention provides a wheelchair with an improved underseat alarm system that enables the wheelchair to be collapsed to a storage position without removing the alarm system. The wheelchair comprises a frame comprising a pair of side frame portions and wheels rotatably connected to the side frame portions for rollingly supporting the frame. The frame further comprises a link assembly movably connecting the side frame portions together for movement between (a) an operative position wherein the side frame portions are spaced apart in a position for facilitating rolling movement of the wheelchair and (b) a storage position wherein the side frame portions are moved inwardly from the operative position adjacent one another for facilitating storage of the wheelchair. A collapsible seat comprises a collapsible seat member connected between the side frame portions in a generally horizontal orientation and a collapsible seat back member connected between the side frame portions in a generally vertical orientation. The collapsible seat member and the collapsible seat back member are extended between the side frame portions in the operative position thereof to enable an occupant to sit on the seat member with a back of the occupant supported by the seat back member. The collapsible seat member and the collapsible seat back member are constructed to collapse in a folding manner between the side frame portions in the storage position thereof for enabling movement of the side frame portions from the operative position thereof to the storage position thereof. The wheelchair further comprises an alarm system comprising an alarm operable to emit a warning signal; an underseat alarm actuator communicated to the alarm; and a collapsible support connected to the alarm actuator.

The collapsible support connects the underseat alarm actuator to the frame so as to mount the underseat alarm actuator such that, when the side frame portions are in the operative position, the alarm actuator is positioned in contact with a bottom surface of the seat member. The collapsible support is constructed to collapse as the side frame portions move to the storage position thereof for enabling movement of the side frame portions from the operative position thereof to the storage position thereof. The alarm actuator is operable such that, when the side frame portions are in the operative position thereof to position the alarm actuator in contact with the bottom surface of the seat member, the alarm actuator senses whether an occupant seated on the seat member is raising his/her weight from the seat member. The alarm is operable to emit the warning signal responsive to the occupant raising his/her weight from the seat member as determined by the alarm actuator.

Another aspect of the invention provides a wheelchair alarm system for a wheelchair that enables the wheelchair to be collapsed without removing the alarm system. The wheelchair comprises (1) a frame comprising a pair of side frame portions and wheels rotatably connected to the side frame portions for rollingly supporting the frame, the frame further comprising a link assembly movably connecting the side frame portions together for movement between (a) an operative position wherein the side frame portions are spaced apart in a position for facilitating rolling movement of the wheelchair and (b) a storage position wherein the side frame portions are moved inwardly from the operative position adjacent one another for facilitating storage of the wheelchair; and (2) a collapsible seat comprising a collapsible seat member connected between the side frame portions in a generally horizontal orientation and a collapsible seat back member connected between the side frame portions in a generally vertical orientation, the collapsible seat member and the collapsible seat back member being extended between the side frame portions in the operative position thereof to enable an occupant to sit on the seat member with a back of the occupant supported by the seat back member. The collapsible seat member and the collapsible seat back member are constructed to collapse in a folding manner between the side frame portions in the storage position thereof for enabling movement of the side frame portions from the operative position thereof to the storage position thereof. The alarm system comprises an alarm operable to emit a warning signal. An underseat alarm actuator is communicatable to the alarm. A collapsible support is connected to the alarm actuator. The collapsible support is constructed to be connected to the frame so as to mount the underseat alarm actuator such that, when the side frame portions are in the operative position, the alarm is positioned in contact with a bottom surface of the seat member. The collapsible support is constructed to collapse as the side frame portions move to the storage position thereof for enabling movement of the side frame portions from the operative position thereof to the storage position thereof. The alarm actuator is operable such that, when the side frame portions are in the operative position thereof to position the alarm actuator in contact with the bottom surface of the seat member, the alarm actuator senses whether an occupant seated on the seat member is raising his/her weight from the seat member. The alarm is operable to emit the warning signal responsive to the occupant raising his/her weight from the seat member as determined by the alarm actuator.

Other objects, features, and advantages of the present invention will become apparent from the following detailed description, the accompanying drawings, and the appended claims.

DETAILED DESCRIPTION OF THE ILLUSTRATED EMBODIMENT

Figure 1:
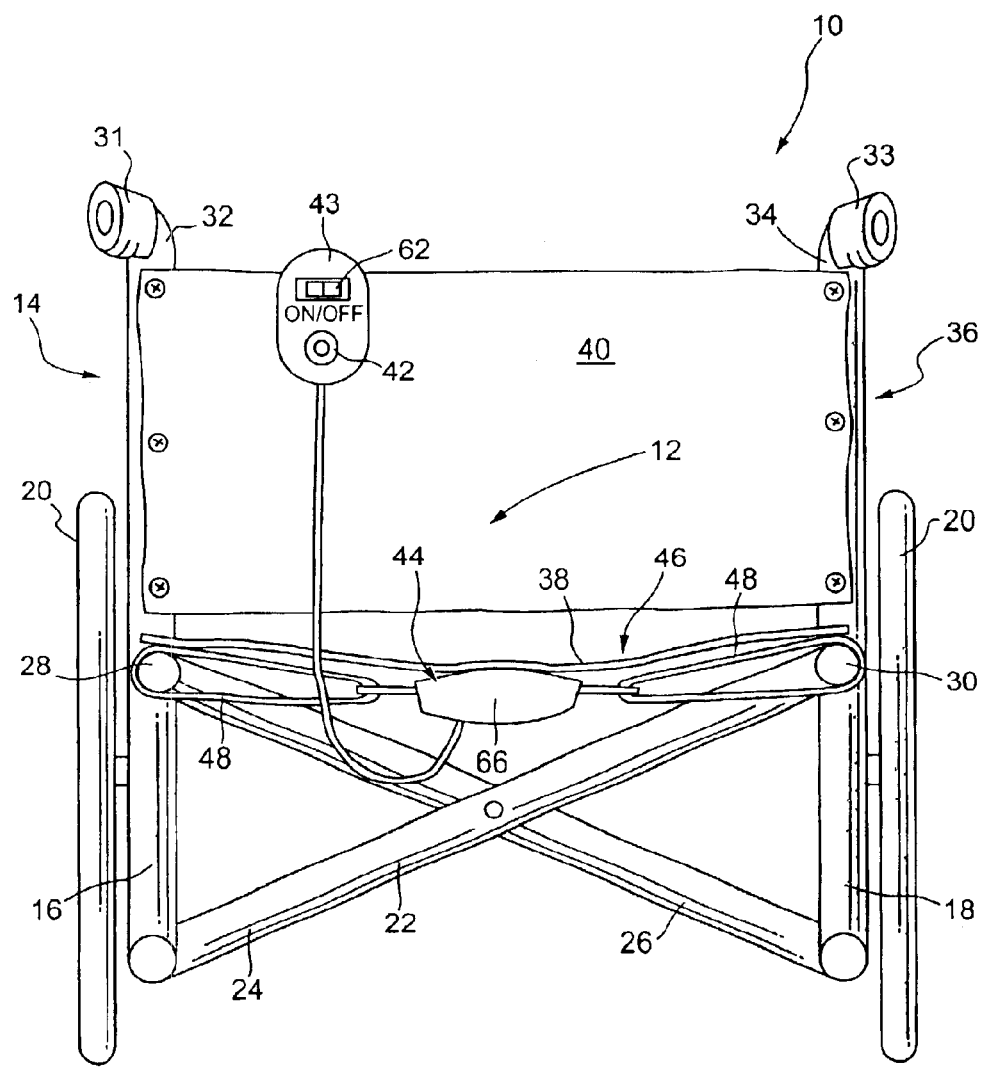
FIG. 1 is a rear view of a wheelchair including an alarm system.
Figure 2:
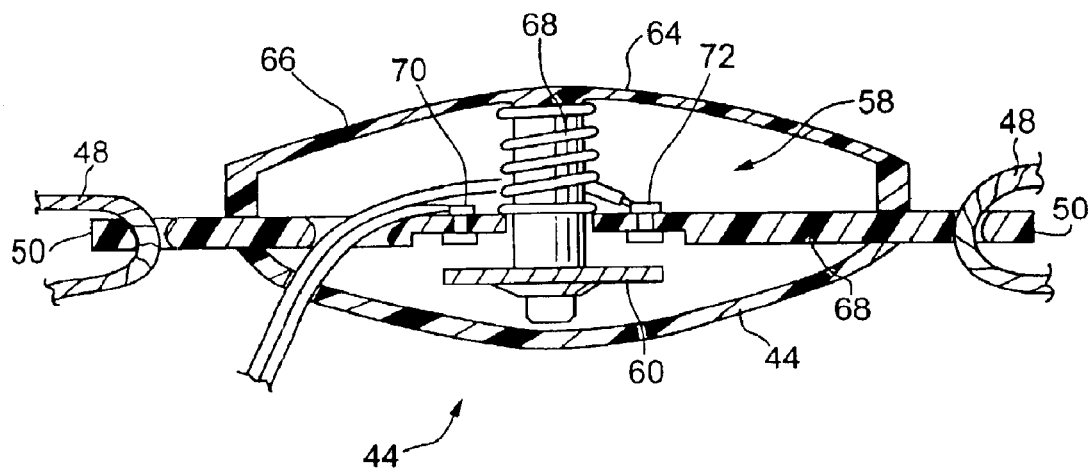
FIG. 2 is a transverse cross-section of the alarm actuator used in the alarm system.
Figure 3:
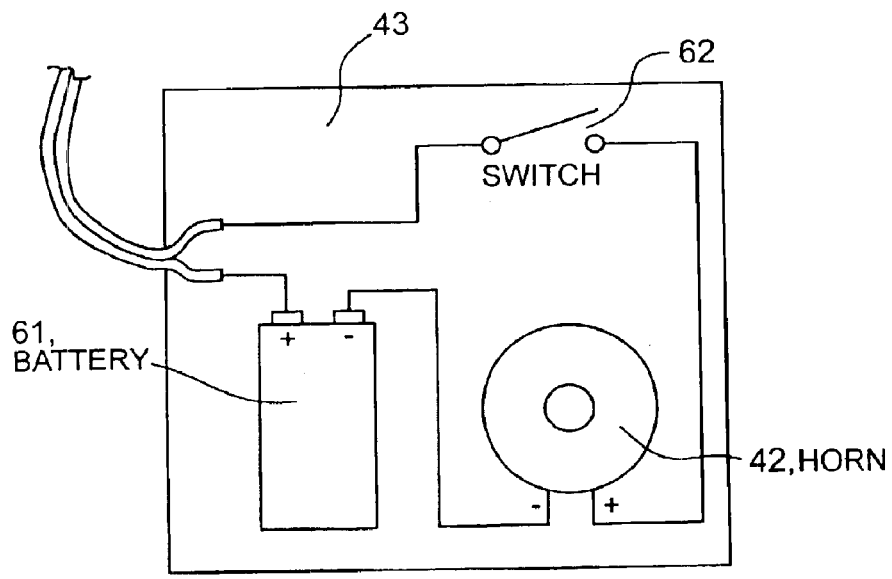
FIG. 3 is a schematic view of the alarm and associated components used in the alarm system.

FIG. 1 illustrates a wheelchair, generally shown at 10. The alarm system, generally indicated at 12 and described in further detail below, may be used on any type of wheelchair, and thus the one described herein is provided solely for illustrative purposes and is not intended to be limiting. The alarm system 12 may be installed in the wheelchair 10 as original equipment (i.e., the wheelchair manufacturer may install it as part of assembly), or it may be a retrofit system design to be installed to existing wheelchairs in the field, or used by those purchasing wheelchairs for purposes of retrofitting prior to usage.

Generally, the wheelchair 10 comprises a frame, generally indicated at 14, comprising a pair of side frame portions 16, 18 and wheels 20 rotatably connected to the side frame portions 16, 18 for rollingly supporting the frame 14. The frame 14 further comprises a link assembly 22 movably connecting the side frame portions 16, 18 together for movement between (a) an operative position (shown in FIG. 1) wherein the side frame portions 16, 18 are spaced apart in a position for facilitating rolling movement of the wheelchair 10 and (b) a storage position wherein the side frame portions 16, 18 are moved inwardly from the operative position adjacent one another for facilitating storage of the wheelchair 10. In the illustrated embodiment, the link assembly 22 is a pair of cross members 24, 26 pivotally connected in a scissors-like manner, but any suitable link assembly may be used for connecting the side frame portions 16, 18 together. The side frame portions 16, 18 each also include fore/aft extending members 28, 30 and generally upright members 32, 34 extending upwardly therefrom. The upper ends of the upright members 32, 34 may be provided with handles 31, 33 for facilitating a person pushing and maneuvering the wheelchair 10 with an occupant therein. The frame 14 has any suitable construction that allows it to be moved between operative and storage positions, and the construction illustrated is not intended to be limiting in any way.

The wheelchair 10 also comprises a collapsible seat, generally indicated at 36, which is comprised of a collapsible seat member 38 connected between the side frame portions 16, 18 in a generally horizontal orientation and a collapsible seat back member 40 connected between the side frame portions 16, 18 in a generally vertical orientation. In the illustrated embodiment, the seat member 38 is fixed to the fore/aft members 28, 30 and the seat back member 40 is fixed to the generally upright members 32, 34. The collapsible seat member 38 and the collapsible seat back member 40 are extended between the side frame portions 16, 18 in the operative position thereof to enable an occupant to sit on the seat member 38 with a back of the occupant supported by the seat back member 40. The collapsible seat member 38 and the collapsible seat back member 40 are constructed to collapse in a folding manner between the side frame portions 16, 18 in the storage position thereof for enabling movement of the side frame portions 16, 18 from the operative position thereof to the storage position thereof. The seat member 38 and the seat back member 40 may be constructed in any manner for enabling them to collapse as the side frame portions 16, 18 are moved to the storage position thereof. For example, they may be made of fabric, a flexible synthetic material, or by a series of interconnected semi-rigid members that enable folding/collapsing. The seat and seat back members 38, 40 may also be padded, or non-padded. The construction and mounting of these members 38, 40 may be done in any suitable fashion and the examples provided herein are not intended to be in any way limiting.

The alarm system 12 comprises an alarm 42, illustrated as an audible horn by way of example, operable to emit a warning signal. The alarm 42 may be mounted anywhere on the wheelchair 10, including on the frame 14 or on the seat 36. In the illustrated embodiment, it is mounted in a housing 43 that is mounted to the upper edge of the seat back member 40 by a removable clip (not shown). As one alternative, the alarm 42 could be integrated into the alarm actuator housing 66, which is discussed below. The warning signal emitted by the alarm 42 may be of any type, such as a visual signal (e.g., a warning light), an audible signal (e.g., a horn or beeping device), or a remote signal (e.g., a signal transmitted to a nursing station for alerting personnel). Generally, the alarm 42 may be of any suitable type and the one illustrated herein is not intended to be limiting.

An underseat alarm actuator 44 is communicated to the alarm 42 and a collapsible support, generally indicated at 46, is connected to the alarm actuator 44. The collapsible support 46 has collapsible support portions 48 extending laterally from the alarm actuator 44. These portions 48 are connected to the side frame portions 16, 18 so as to mount the underseat alarm actuator 44 such that, when the side frame portions 16, 18 are in the operative position, the alarm actuator 44 is positioned in contact with a bottom surface of the seat member 38. The collapsible support portions 48 are also constructed to collapse in a folding manner between the side frame portions 16, 18 in the storage position thereof for enabling movement of the side frame portions 16, 18 from the operative position thereof to the storage position thereof. The collapsible support 46 may have any suitable construction for mounting the actuator 44 in its operating position beneath the seat member 38 and the illustrated embodiment is not intended to be limiting. For example, the portions 48 may be chains that bolt or clip onto any part of the side frame portions; straps with hook and loop type fasteners (e.g., VELCRO®) at the ends for looping onto the fore/aft members 28, 30, or any other part of the side frame portions 16, 18; or straps that fasten, by clipping or looping, to the side frame portions 16, 18, or including the fore/aft members 28, 30 thereof.

Also, instead of using two support portions that collapse in a folding manner, the support 46 could be provided by a rigid arm that is spring biased to support the actuator 44 in is operating position when the side frame portions 16, 18 are in their operative position. The arm could be constructed to pivot or fold downwardly to affect collapsing thereof as the side frame portions 16, 18 are moved to the storage position without having to remove the alarm system 12 from the wheelchair 10.

In the illustrated embodiment, the collapsible support portions 48 are flexible straps constructed to be connected to the side frame portions 16, 18, and particularly the fore/aft members 28, 30. Optionally, the flexible belts 48 include adjusters (not shown) for enabling lengths of the flexible belts 48 to be adjusted to position the alarm actuator 44 in contact with a bottom surface of the seat member 38 when the side frame portions 16, 18 are in the operative positions thereof. Further optionally, the adjusters are fastening buckles constructed to have main portions of the flexible straps 48 pass therethough and to have attaching portions of the flexible straps 48 looped around parts of the side frame portions (preferably the fore/aft members 28, 30) pass back therethrough in a secure relation for adjustably securing the straps 48 to the side frame portions 16, 18, thus enabling the actuator 44 to be properly positioned beneath the seat member 38 in contact therewith.

The inner ends of the straps 48 may be attached to strap receiving loops 50 extending from the actuator housing 66. In the illustrated embodiment, these loops 50 are integrally formed with a molded plastic base plate 68, discussed below.

Any other suitable construction for attaching these straps 48, however, may be used.

The alarm actuator 44 is operable such that, when the side frame portions 16, 18 are in the operative position thereof to position the alarm actuator 44 in contact with the bottom surface of the seat member 38, the alarm actuator 44 senses whether an occupant seated on the seat member is raising his/her weight from the seat member 38. That is, this allows the actuator 44 to determine whether the occupant is attempting to rise, or has risen from, the seat 36. The alarm 42 is operable to emit the warning signal responsive to the occupant raising his/her weight from the seat member 38, as determined by the actuator 44.

Any type of alarm actuator 44 may be used, and in the illustrated embodiment the alarm actuator 44 is an electrical switch 58 communicated to the alarm 42 by electroconductive wiring. The switch 58 illustrated is of the type comprising a contact element 60 that is pushed downwardly to an off-state by occupant weight on the seat member 38. This prevents current from flowing through the switch 58, and the alarm will not emit the warning signal so long as this current continues to be interrupted. The current is provided by one or more batteries 61 stored in the housing 43 (as illustrated) or the actuator housing 64.

In the illustrated embodiment, the contact element 60 is connected to a flexible fabric or plastic upper wall 64 of the alarm actuator housing 66. The upper wall 64 contacts the bottom surface of the seat member 38 and a spring 68 biases the wall 64 and contact element 60 upwardly. The base plate 68 has two terminals 70, 72, one connected to the battery 61 and the other to the alarm 42. When the contact element 60 is moved downwardly by an occupant's weight on seat member 38, the contact element 60 is disengaged from the terminals 70, 72 (i.e., the off-state), and current is interrupted, thus preventing actuation of the alarm 42. When the occupant raises his/her weight from the seat member 30, the spring 68 urges the upper wall 64 and the contact element 60 upwardly so that the contact element 60 contacts the terminals 70, 72 and closes the circuit (i.e., the on-state). This allows current to flow, thereby actuating the alarm 42 to emit its warning signal. Alternatively, switch 58 could have any other construction, such as, for example, one using a leaf spring type contact element that is self-biased to an off-state interrupting the current flow, and the alarm 42 would be adapted to emit its warning signal responsive to the interruption of current flow. An occupant sitting on seat member 38 would force the contact element downwardly to close the circuit, thus keeping the alarm 42 from activating. Further, any other suitable construction for the alarm actuator 44 may be used and the examples provided herein should not be considered limiting in any way.

Preferably, but optionally, the alarm system 12 further comprises an on-off switch 62 for activating and deactivating the alarm system 12. This allows the health care person handling the wheelchair 10 to deactivate the alarm system 12 prior to allowing the occupant to leave the chair, which avoids the alarm 12 emitting the warning signal unnecessarily. The on-off switch 62 is preferably located somewhere difficult for the occupant to reach, such as on the back of the wheelchair 10 or underneath the wheelchair 10. The on-off switch 62 may be integrated into the alarm housing 43 or the alarm actuator housing 66, or may be provided as a separate component. As illustrated, it is integrated into the alarm housing 43, and deactivates the alarm 42 by interrupting the circuit discussed above.

The foregoing illustrated embodiment has been provided solely for the purposes of illustrating the structural and functional principles of the present invention and is not intended to be limiting. To the contrary, the present invention is intended to encompass all modifications, substitutions, alterations and equivalents within the spirit and scope of the appended claims.

What is claimed:

1. A wheelchair comprising:
   a frame comprising a pair of side frame portions and wheels rotatably connected to the side frame portions for rollingly supporting the frame, the frame further comprising a link assembly movably connecting the side frame portions together for movement between (a) an operative position wherein the side frame portions are spaced apart for facilitating rolling movement of the wheelchair and (b) a storage position wherein the side frame portions are moved inwardly from the operative position adjacent one another for facilitating storage of the wheelchair;
   a collapsible seat comprising a collapsible seat member connected between the side frame portions in a generally horizontal orientation and a collapsible seat back member connected between the side frame portions in a generally vertical orientation, the collapsible seat member and the collapsible seat back member being extended between the side frame portions in the operative position thereof to enable an occupant to sit on the seat member with a back of the occupant supported by the seat back member, the collapsible seat member and the collapsible seat back member being constructed to collapse in a folding manner between the side frame portions in the storage position thereof for enabling movement of the side frame portions from the operative position thereof to the storage position thereof; and
   an alarm system comprising:
   an alarm operable to emit a warning signal;
   an underseat alarm actuator communicated to the alarm; and
      a collapsible support connected between the alarm actuator and the frame so as to mount the alarm actuator such that, when the side frame portions are in the operative position, the alarm actuator is positioned in contact with a bottom surface of the seat member, the collapsible support being constructed to collapse as the side frame portions move to the storage position thereof for enabling movement of the side frame portions from the operative position thereof to the storage position thereof;
      the alarm actuator being operable such that, when the side frame portions are in the operative position thereof to position the alarm actuator in contact with the bottom surface of the seat member, the alarm actuator senses whether an occupant seated on the seat member is raising his/her weight from the seat member;
      the alarm being operable to emit the warning signal responsive to the occupant raising his/her weight from the seat member as determined by the alarm actuator.

2. A wheelchair according to claim 1, wherein the collapsible support has collapsible support portions extending laterally from the alarm actuator and being connected to the side frame portions, the collapsible support portions being constructed to collapse in a folding manner between the side frame portions as the side frame portions move to the storage position thereof.

3. A wheelchair according to claim 2, wherein the warning signal is selected from the group consisting of an audible signal, a visual signal, and a wireless signal to a remote device.

4. A wheelchair according to claim 2, wherein the alarm actuator is an electrical switch communicated to the alarm.

5. A wheelchair according to claim 4, wherein the switch comprises a contact element positioned so as to be pushed downwardly to an off-state by occupant weight on the seat member and being biased to an on-state upon the occupant weight being raised from the seat member, the alarm being operable to emit the warning signal responsive to the contact element moving to the on-state thereof.

6. A wheelchair according to claim 2, wherein the alarm system further comprises an on-off switch for activating and deactivating the alarm system.

7. A wheelchair according to claim 5, wherein the alarm system further comprises an on-off switch for activating and deactivating the alarm system.

8. A wheelchair according to claim 2, wherein the collapsible support portions comprise flexible straps constructed to be connected to the side frame portions.

9. A wheelchair according to claim 8, wherein the flexible straps include adjusters for enabling lengths of the flexible straps to be adjusted to position the alarm actuator in contact with a bottom surface of the seat member when the side frame portions are in the operative positions thereof.

10. A wheelchair according to claim 5, wherein the collapsible support portions comprise flexible straps constructed to be connected to the side frame portions.

11. A wheelchair according to claim 10, wherein the flexible straps include adjusters for enabling lengths of the flexible straps to be adjusted to position the alarm actuator in contact with a bottom surface of the seat member when the side frame portions are in the operative position thereof.

12. A wheelchair alarm system for a wheelchair, the wheelchair comprising: (1) a frame comprising a pair of side frame portions and wheels rotatably connected to the side frame portions for rollingly supporting the frame, the frame further comprising a link assembly movably connecting the side frame portions together for movement between (a) an operative position wherein the side frame portions are spaced apart for facilitating rolling movement of the wheelchair and (b) a storage position wherein the side frame portions are moved inwardly from the operative position adjacent one another for facilitating storage of the wheelchair; and (2) a collapsible seat comprising a collapsible seat member connected between the side frame portions in a generally horizontal orientation and a collapsible seat back member connected between the side frame portions in a generally vertical orientation, the collapsible seat member and the collapsible seat back member being extended between the side frame portions in the operative position thereof to enable an occupant to sit on the seat member with a back of the occupant supported by the seat back member, the collapsible seat member and the collapsible seat back member being constructed to collapse in a folding manner between the side frame portions in the storage position thereof for enabling movement of the side frame portions from the operative position thereof to the storage position thereof; the alarm system comprising:

an alarm operable to emit a warning signal;

an underseat alarm actuator communicatable to the alarm; and a collapsible support connected to the alarm actuator, the collapsible support being constructed to be connected to the frame so as to mount the underseat alarm actuator such that, when the side frame portions are in the operative position, the alarm actuator is positioned in contact with a bottom surface of the seat member, the collapsible support being constructed to collapse as the side frame portions move to the storage position thereof for enabling movement of the side frame portions from the operative position thereof to the storage position thereof;

the alarm actuator being operable such that, when the side frame portions are in the operative position thereof to position the alarm actuator in contact with the bottom surface of the seat member, the alarm actuator senses whether an occupant seated on the seat member is raising his/her weight from the seat member;

the alarm being operable to emit the warning signal responsive to the occupant raising his/her weight from the seat member as determined by the alarm actuator.

13. A wheelchair alarm system according to claim 12, wherein the collapsible support has collapsible support portions extending laterally from the alarm actuator for connection to the side frame portions of the wheelchair frame, the collapsible support portions being constructed to collapse in a folding manner between the side frame portions as the side frame portions move to the storage position thereof.

14. A wheelchair alarm system according to claim 13, wherein the warning signal is selected from the group consisting of an audible signal, a visual signal, and a wireless signal to a remote device.

15. A wheelchair alarm system according to claim 13, wherein the alarm actuator is an electrical switch communicated to the alarm.

16. A wheelchair alarm system according to claim 15, wherein the switch comprises a contact element positioned to be pushed downwardly to an off-state by occupant weight on the seat member and being biased to an on-state upon the occupant weight being raised from the seat member, the alarm being operable to emit the warning signal responsive to the contact element moving to the on-state thereof.

17. A wheelchair alarm system according to claim 13, wherein the alarm system further comprises an on-off switch for activating and deactivating the alarm system.

18. A wheelchair alarm system according to claim 16, wherein the alarm system further comprises an on-off switch for activating and deactivating the alarm system.

19. A wheelchair alarm system according to claim 13, wherein the collapsible support portions comprise flexible straps constructed to be connected to the side frame portions.

20. A wheelchair alarm system according to claim 19, wherein the flexible straps include adjusters for enabling lengths of the flexible straps to be adjusted to position the alarm actuator in contact with a bottom surface of the seat member when the side frame portions are in the operative position thereof.

21. A wheelchair alarm system according to claim 16, wherein the collapsible support portions comprise flexible straps constructed to be connected to the side frame portions.

22. A wheelchair alarm system according to claim 21, wherein the flexible straps include adjusters for enabling lengths of the flexible straps to be adjusted to position the alarm actuator in contact with a bottom surface of the seat member when the side frame portions are in the operative positions thereof.

* * * * *